United States Patent [19]

Taylor, Jr. et al.

[11] Patent Number: 5,637,778
[45] Date of Patent: Jun. 10, 1997

[54] ISOPROPYL ALCOHOL AND DIISPROPYL ETHER PRODUCTION FROM CRUDE BY-PRODUCT ACETONE IN ONE STEP

[75] Inventors: Robert J. Taylor, Jr.; Pei-Shing E. Dai, both of Port Arthur; John F. Knifton, Austin; Bobby R. Martin, Beaumont, all of Tex.

[73] Assignee: Texaco Chemical Inc., White Plains, N.Y.

[21] Appl. No.: 287,451

[22] Filed: Aug. 8, 1994

[51] Int. Cl.$^6$ ................................................. C07C 41/09
[52] U.S. Cl. ................................................. 568/698
[58] Field of Search ................................................. 568/698

[56] References Cited

U.S. PATENT DOCUMENTS

| | | |
|---|---|---|
| 3,904,550 | 9/1975 | Lloyd . |
| 3,953,517 | 4/1976 | Schmitt et al. . |
| 3,955,939 | 5/1976 | Sommer et al. . |
| 4,364,839 | 12/1982 | McDaniel et al. . |
| 4,364,864 | 12/1982 | Beffa et al. . |
| 4,382,878 | 5/1983 | Kehl . |
| 4,397,765 | 8/1983 | McDaniel . |
| 4,424,139 | 1/1984 | McDaniel et al. . |
| 4,440,871 | 4/1984 | Lok et al. . |
| 4,504,638 | 3/1985 | McDaniel et al. . |
| 4,524,225 | 6/1985 | Qualeatti et al. . |
| 4,528,414 | 7/1985 | Long et al. . |
| 4,538,008 | 8/1985 | Firth et al. . |
| 4,547,479 | 10/1985 | Johnson . |
| 4,596,862 | 6/1986 | McDaniel et al. . |
| 4,822,921 | 4/1989 | Knifton et al. . |
| 4,827,048 | 5/1989 | Knifton . |
| 4,906,787 | 3/1990 | Huang et al. . |
| 4,910,329 | 3/1990 | McDade . |
| 5,001,102 | 3/1991 | Wells . |
| 5,017,729 | 5/1991 | Fukuhara et al. . |
| 5,059,724 | 10/1991 | Chen et al. . |
| 5,059,725 | 10/1991 | Knifton et al. . |
| 5,081,318 | 1/1992 | Knifton . |
| 5,099,072 | 3/1992 | Knifton . |
| 5,144,061 | 9/1992 | Hoelderich et al. . |
| 5,144,086 | 9/1992 | Harandi et al. . |
| 5,157,161 | 10/1992 | Knifton . |
| 5,157,162 | 10/1992 | Knifton . |
| 5,162,592 | 11/1992 | Knifton et al. . |
| 5,183,947 | 2/1993 | Knifton et al. . |
| 5,189,182 | 2/1993 | Kummer et al. . |
| 5,208,387 | 5/1993 | Harandi et al. . |

*Primary Examiner*—Jose'G. Dees
*Assistant Examiner*—Rosalynd A. Williams
*Attorney, Agent, or Firm*—James L. Bailey; Kenneth R. Priem; Cynthia L. Hunter

[57] ABSTRACT

Disclosed is a one-step method for synthesis of methyl tertiary butyl ether, diisopropyl ether and isopropyl ether from crude streams containing acetone, methanol and t-butyl alcohol which comprises reacting an acetone-rich feed over a bifunctional catalyst comprising 5–45% by weight of a catalyst consisting essentially of a hydrogenation catalyst selected from the group consisting of one or more metals selected from the group consisting of IB, VIB or VIII of the Periodic Table and a heteropoly acid on a 55%–95% of the total weight of the catalyst of a support comprising a compound selected from the group consisting of:

a. a metal phosphate;

b. 5 to 95% by weight metal phosphate supported on 95 to 5 wt % Group III or IV oxide; and c. a large pore silicoaluminophosphate.

17 Claims, 1 Drawing Sheet

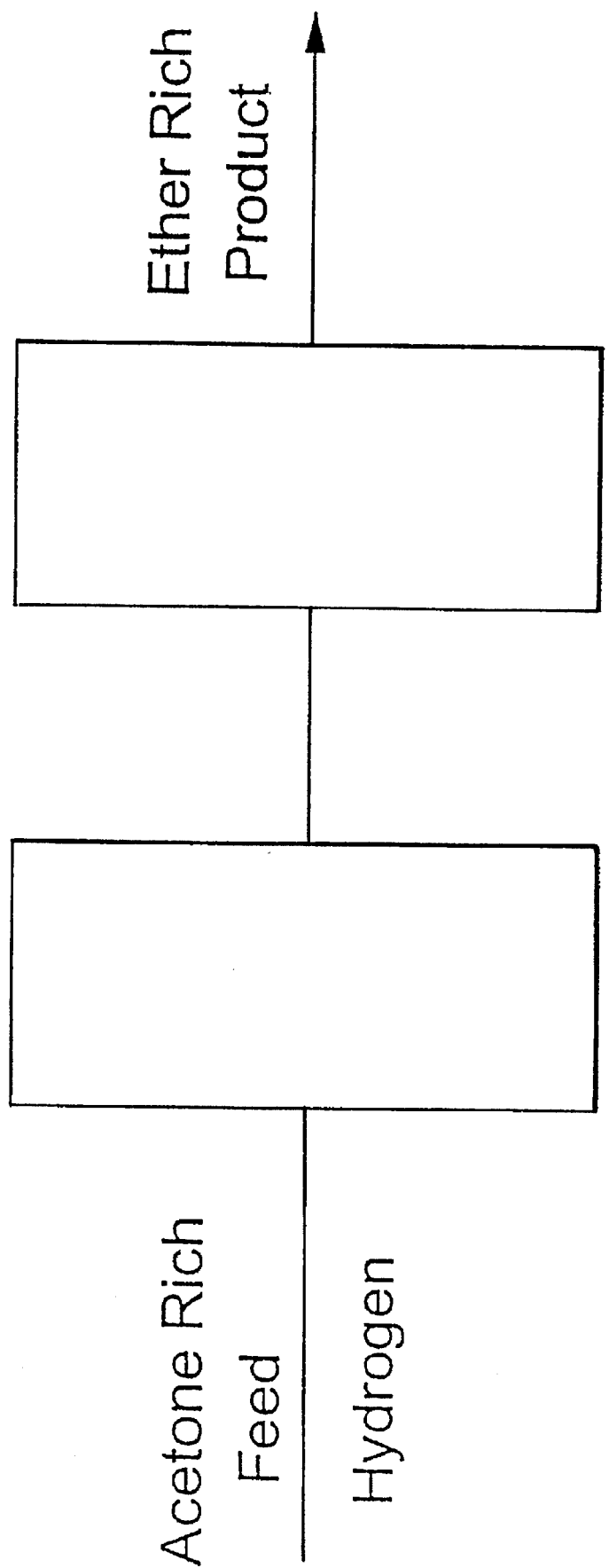

ISOPROPYL ALCOHOL AND DIISPROPYL ETHER PRODUCTION FROM CRUDE BY-PRODUCT ACETONE IN ONE STEP

CROSS-REFERENCE

This application is related to U.S. Ser. Nos. 08/096,873; 08/057,373; U.S. Pat. No. 5,364,981 and U.S. Application Ser. No. 08/188,007. It is also related to U.S. Pat. Nos. 4,822,921; 4,827,048; 5,099,072; 5,081,318; 5,059,725; 5,157,162; 5,162,592; 5,157,161; 5,183,947; and 5,313,006; 5,214,217; 5,214,218; 5,220,078; 5,338,890; 5,364,981; and 5,352,847; all of which are incorporated by reference herein in their entirety.

FIELD OF THE INVENTION

This invention concerns a novel one-step integrated procedure for production of high octane blending components for reformulated gasoline from a crude by-product acetone stream which comprises reacting the crude acetone stream over a bifunctional catalyst to give an effluent-rich in diisopropyl ether (DIPE), methyl t-butyl ether (MTBE) and isopropyl t-butyl ether (IPTBE). The bifunctional (hydrogenation/etherification) catalyst comprises a hydrogenation catalyst on a non-zeolitic support comprising a metal phosphate.

BACKGROUND OF THE INVENTION

It is known to those skilled in the art that ethers, including both symmetrical and unsymmetrical ethers, may be prepared by reacting an alcohol with another alcohol to form the desired product. The reaction mixture, containing catalyst and/or condensing agent may be separated and further treated to permit attainment of the desired product. Such further treatment commonly includes one or more distillation operations.

Hydrogenation catalysts are known and are generally selected from Group VIII of the Periodic Table. Suitable metals include, but are not limited to, platinum, palladium, tin, nickel and copper alone, or in combination.

In U.S. Pat. No. 3,955,939 to Sommer et al. (1976), there is disclosed the production of a water-free mixture of isopropyl alcohol, diisopropyl alcohol, diisopropyl ether and by-products by the catalytic hydration of propylene in the gaseous phase at temperatures of 140°–170° C., wherein the water-free mixture formed according to the process can be used directly as an additive to gasoline fuel.

Conversion of acetone to MIBK is addressed in U.S. Pat. No. 3,953,517. The catalyst is a noble metal. In U.S. Pat. No. 5,059,724 a method is disclosed for the selective production of methyl isobutyl ketone.

In U.S. Pat. No. 5,017,729 there is disclosed a multistage process for producing phenol, wherein acetone is hydrogenated in the fourth step.

Phosphate catalysts are known in the art. Among such materials are aluminum phosphates, both stoichiometric $AlPO_4$ and non-stoichiometric $Al(PO_4)_x$ where x is less than 1. For instance, U.S. Pat. No. 3,904,550 describes the preparation of such materials and their use as desulfurization catalysts. U.S. Pat. No. 3,801,704 teaches that aluminum phosphates can be used for catalytic dehydration. U.S. Pat. No. 4,524,225 demonstrates that such phosphates also function as hydrogenation catalysts. Other cited uses of aluminum phosphates include cracking (U.S. Pat. No. 4,382,878), ether rearrangement (U.S. Pat. No. 4,538,008), and polyolefin synthesis (U.S. Pat. Nos. 4,364,839; 4,547,479; 4,424,139; 4,397,765; 4,596,862; 4,504,638; and 4,364,864). In all of these cases stoichiometric or non-stoichiometric aluminum phosphates are taught and methods for making them described.

U.S. 5,189,182 discloses a method of preparation of 5-methyl butyrolactone over a zeolite and/or one of several phosphate catalysts, including silica aluminum phosphate (SAPO).

The use of catalysts of the formula $M(PO_4)_y X'$ wherein M is a transition metal, X' is an anionic species and y is from about 0.1 to about 0.9 is disclosed in U.S. Pat. No. 4,910,329 as useful in the preparation of hydroxyalkyl esters of acrylic and methacrylic acid.

In U.S. Pat. No. 5,001,102, there is also disclosed the use of iron phosphate catalysts in the production of unsaturated hydroxyalkyl esters.

In U.S. Pat. No 5,144,061 it is disclosed that, in addition to certain zeolites, aluminum phosphates can be used as catalysts for preparing alkene carboxylic acid esters.

Silicoaluminophosphates are also known in the art. Early attempts to prepare them occurred during research efforts to isomorphously replace a portion of the $SiO_2$ tetrahedra of zeolitic aluminosilicates with $PO_2$ tetrahedra during the synthesis process. Barrer et al. (J. Chem. Soc. 1965, pp. 6616–6628).

No evidence of isomorphous substitution of phosphorus for silicon was found, although in U.S. Pat. 3,443,892 there is disclosed the preparation of a faujasite-type zeolite containing P2O5®Substantial success in preparing zeolite analogues containing phosphorus was reported by Flanigen and Grose, Molecular Sieve Zeolites-I, ACS, Washington, D.C. (1971), using synthesis technique utilizing gel crystallization involving controlled copolymerization and coprecipitation of all the framework component oxides.

In U.S. Pat. No. 4,440,871 there is disclosed a novel class of silicon-substituted aluminophosphates which are both crystalline and microporous and exhibit properties which are characteristic of both the aluminosilicate zeolites and aluminophosphates which have a three-dimensional microporous crystal framework structure of $PO_2^+$, $AlO_2^-$ and $SiO_2$ tetrahedral units.

In U.S. Pat. No. 4,528,414 there is disclosed a process for the oligomerization of linear and/or branched chain $C_2$ to $C_{12}$ olefins with non-zeolitic molecular sieves of the description just mentioned above in U.S. Pat. No. 4,440,871.

Non-zeolitic molecular sieves, identified by the acronyms SAPO, TAPO, MeAPO and FAPO are described and explained in U.S. Pat. No. 4,440,871 (SAPOs), incorporated herein by reference and in U.S. Pat. Nos. 4,500,651 (TAPOs), 4,567,029 (MeAPOs) and 4,554,143 (FAPOs).

In European Patent 323138 and U.S. Pat. No. 4,906,787, there is disclosed a catalytic process for converting light olefins to ethers suitable as high octane blending stocks carried out by contacting the olefin, especially propene, with water and alcohol recovered from a downstream distillation operation in an olefin conversion unit in the presence of an acidic zeolite catalyst. In this work diisopropyl ether (DIPE) was prepared from $C_3H_6$ and aqueous iso-PrOH in the presence of silica-bound zeolite Beta catalyst at 166°.

In another European Patent, EP 323268, light olefins are converted to alcohols and/or ethers in the presence of β-zeolite.

In U.S. Pat. No. 5,144,086, to Harandi et al., there is disclosed an integrated multistage process for the production of diisopropyl ether and substantially pure propene wherein in the second stage isopropanol containing about 0%–20% water is contacted with an acidic large pore zeolite etherification catalyst which comprises a β-zeolite having a Si:Al ratio of about 30:1 to 50:1.

In U.S. Pat. No. 5,208,387, also to Harandi et al., there is disclosed a process for the acid catalyzed production of DIPE from propene and water feed stream that eliminates the propene recycle stream to the olefin hydration reactor and achieves high propene conversion. This process is carried out in two stages wherein the first stage comprises a zeolite catalyzed hydration and etherification of propene employing a minimum of water feed and the second stage converts unconverted propene from the first stage reactor by hydration and etherification to DIPE.

In an article titled "Race to License New MTBE and TAME Routes Heats Up", Rotman, D., *Chemical Week*, Jan. 6, 1993, p. 48, there is a review of new technology at several different companies which centers around skeletal isomerization, particularly of $C_4$ and $C_5$ olefins. The interest in this technology is fueled by the promise of dramatically increased and relatively inexpensive isobutylene and isoamylene that could boost MTBE and TAME production, often constrained by the amounts of available isobutylene in refinery or steam cracker streams. DIPE production from propylene is also discussed.

Mobil Corp. has disclosed new etherification technology that can produce fuel oxygenates based only on olefinic refinery streams and water. This process has the potential to allow refiners to produce oxygenates without having to rely on an external supply of alcohols. The technology is developed around diisopropyl ether (DIPE) based on propylene. The DIPE has similar physical and blending activities to MTBE and TAME and is a perfectly acceptable fuel oxygen source. Wood, A., *Chemical Week*, Apr. 15, 1992, p. 7.

None of the available references would suggest the combination of a bifunctional catalyst comprising one or more metals from Group IB, VIB or VIII on one of several classes of phosphate catalysts for the one-step conversion of low value crude acetone in a by-product stream into useful oxygenate products. The portion of said by-product stream which typically comprises acetone is about 20% to 80%. It would greatly enhance the economics of any process to produce MTBE or other oxygenates if acetone from a by-product stream could be converted in one step to useful oxygenate products which could be fractionated to isolate diisopropyl ether (DIPE) and isopropyl tertiary butyl ether (IPTBE).

SUMMARY OF THE INVENTION

In accordance with the foregoing, the novel method of the instant invention for the generation of diisopropyl ether and isopropyl t-butyl ether in one step from a crude by-product acetone stream comprises reacting an acetone-rich feed over a heterogeneous catalyst comprising 5%–45% by weight hydrogenation selected from one or more metals selected from the group consisting of Group IB, VIB or VIII or selected from heteropoly acids supported on a dehydration/etherification catalyst comprising 55% to 95% by weight of a support selected from the group consisting of:

a. a metal phosphate;

b. 5 to 95 wt % metal phosphate supported on 95 to 5 wt % Group III or IV oxide;

c. a large pore silicoaluminophosphate.

DESCRIPTION OF THE DRAWING

The drawing represents the one-step hydrogenation/etherification of the instant invention.

DETAILED DESCRIPTION OF THE PREFERRED EMBODIMENT

In the production of high octane blending components for reformulated gasoline such as diisopropyl ether (DIPE), methyl t-butyl ether (MTBE) and isopropyl t-butyl ether (IPTBE) by the method outlined below, the by-product acetone stream contains, in addition significant quantities, that is, preferably greater than 5% of both methanol (MeOH) and t-butanol (tBA). For the cogeneration of DIPE, MTBE and IPTBE, the crude acetone feed preferably contains 10%–40% each of both methanol and t-butanol.

The one-step synthesis can be represented by:

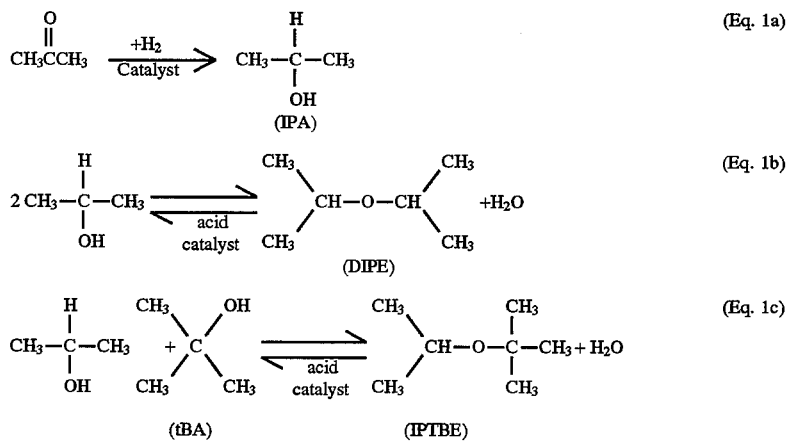

In a process to make propylene oxide a large number of by-products are typically generated with the desired product. The by-products may include formic acid, acetic acid, t-butanol and acetone. The acetone may constitute about 20% to 80% of certain crude by-product streams. These crude acetone streams may be further mixed with methanol.

The object of the invention is to upgrade low-value crude acetone to IPA and ethers (MIPE, DIPE, MTBE, IPTBE). In a PO/MTBE unit, two typical waste streams of acetone would include one from the TBHP (tertiary butyl hydroperoxide) concentration column and one from the tBA (t-butyl alcohol) purification column overhead. The following compositions are typical of these respective crude acetone streams:

TBHP concentration column distillate in weight percent:
2.3% methyl formate (MF)

14.8% acetone
1.8% methanol
76.4% t-butanol
3.0% di-t-butyl peroxide (DTBP)
TBA purification column overhead product
1.1% isobutane
11.6% methyl formate
72.7% acetone
10.0% methanol
1.7% t-butanol
1.3% di-t-butyl peroxide It is important to point out that methyl formate and di-t-butyl peroxide are poisons to hydrogenation catalysts. A number of NiCu catalysts based on zeolite/alumina deactivated rapidly with peroxide-containing feedstocks in the one-step synthesis of MTBE.

In related art, it is known to produce IPA and DIPE by the hydration of propylene and subsequent etherification of IPA. The instant invention allows the production of IPA and DIPE as well as other ethers such as MTBE and IPTBE from crude acetone containing tBA and MeOH in one-step in the presence of a bifunctional catalyst and hydrogen.

The conversion of acetone to isopropyl alcohol is a very exothermic reaction. When catalysts having high acidity are used for this conversion, there is the potential for a runaway reaction which further converts the IPA to propylene and then reduces the propylene to propane in another exothermic reaction. It is therefore advantageous to have a catalyst which does not promote this further conversion of IPA to propylene. It is desirable to have a catalyst which has some activity for conversion of the IPA to DIPE.

The selection of a catalyst with the proper activity to hydrogenate acetone to IPA, convert some IPA to DIPE and not convert IPA to propylene is critical. The bifunctional catalyst of the instant invention comprises 5%–45% by weight hydrogenation catalyst consisting essentially of one or more metals from the group consisting of nickel, copper, platinum, palladium, tin and copper or a heteropoly acid deposited on 55% to 95% of the total catalyst weight of a support consisting essentially of a metal phosphate alone or in combination with an oxide support from the group consisting of $SiO_2$ and $Al_2O_3$. In another embodiment the support can comprise large pore silicoaluminophosphates, such as, for example, SAPO-5, SAPO-37 and metal-substituted SAPOs, such as MeAPSO-36, where Me=Mg, Zn, Co, and Fe.

As noted, hydrogenation portion of the catalyst comprises one or more metals selected from Group IB, VIB or VIII of the Periodic table. The total percent by weight of the portion of the catalyst comprising a hydrogenation catalyst is preferably between 5 wt % and 45 wt %. The hydrogenation portion of the catalyst may comprise one or more metals selected from the group consisting of platinum, palladium, nickel, copper, tin and chromium. A preferred combination is nickel, copper and chromium, where the total metal content of Ni/Cu/Cr is in the range of 20 wt % to 90 wt % and preferably 30% to 85%. The catalyst contains between 15 wt % and 70 wt %, preferably 20%–50% and particularly about 43% Ni, a loading of copper of 3 wt % to 25 wt %, preferably about 16% and, optionally, a loading of Cr of 0.5 to 5 wt %, preferably about 2 wt %.

Example 1, using the Ni/Cu/Cr/iron phosphate catalyst, shows high conversion of the acetone with high liquid yield and good selectivity to IPA/DIPE. The catalyst of Example 2 shows a catalyst prepared with a non-acidic molecular sieve which has a very low acidity. This catalyst shows good activity for conversion of acetone to IPA but gives less than 1% DIPE in the product. The catalyst of Example 3 shows a catalyst which has too high an activity for the conversion of IPA to propylene. In this case, a very large liquid yield loss results from the conversion of acetone to propylene. The majority of the liquid product resulting from this catalyst was water, a by-product from the conversion of acetone to propylene.

In some cases it is useful to include chromium with nickel and copper. When employed, an amount of about 1 wt % to 5 wt % is appropriate, preferably about 2 wt %.

The heteropoly acids which are effective in the subject reaction comprise a class of acids formed by the condensation of two or more inorganic oxyacids. For example, phosphate and tungstate ions, when reacted in an acidic medium, are condensed to form 12-tungstophosphoric acid, a typical heteropoly acid (HPA) according to Equation 2:

$$PO_4^{3-} + 12WO_4^{2-} + 27H^+ \rightarrow H_3PW_{12}O_{40} + 12H_2O \qquad \text{(Eq. 2)}$$

A wide variety of elements ranging from Group I to Group VIII can become the central atom of the HPA anion, or the heteroatom as it is called (P in the case of Eq. 2). The nature of the heteroatom is a governing factor which determines both the condensation structure and the physical properties of the HPA.

Atoms coordinated to the heteroatom via oxygens are called polyatoms (W in the case of Equation 2) and in most cases are any one of such limited species as molybdenum, tungsten, niobium and vanadium. In the case of molybdenum (Mo) as the polyatom, the nature of the heteroatoms, condensation ratios and chemical formulae of the corresponding HPA anions are summarized in Table I.

Anions containing the so-called Keggin structure have a condensation ratio of 1:12 and are the most typical of all HPA anions. Heteropoly acids with the Keggin structure, and their homologues, are generally the most readily available HPA's and the ones most commonly used in catalysis. The synthesis of these HPA's is well documented in the literature [see for example U.S. Pat. No. 3,947,332 (1976)].

TABLE I

Typical heteropolymolybdate anions

| CONDENSATION RATIOS | | HETERO ATOMS (X) | CHEMICAL FORMULAS |
| --- | --- | --- | --- |
| 1:12 | Keggin structure | $P5+$, $As^{5+}$, $Si^{4+}$, $Ge^{4+}$ | $[X^{n+}Mo_{12}O_{40}]^{-(8-n)}$ |
| | Silverton structure | $Ce^{4+}$, $Th^{4+}$ | $[X^{4+}Mo_{12}O_{42}]^{8-}$ |
| 1:11 | Keggin structure (decomposition) | $P^{5+}$, $As^{5+}$, $Ge^{4+}$, $Si^{4+}$ | $[X^{n+}Mo_{11}O_{39}]^{-(12-n)}$ |
| 2:18 | Dawson structure | $P^{5+}$, $As^{5+}$ | $[X_2^{5+}Mo_{18}O_{62}]^{6-}$ |
| 1:9 | Waugh structure | $Mn^{4+}$, $Ni^{4+}$ | $[X^{4+}Mo_9O_{32}]^{6-}$ |
| 1:6 | Anderson structure (A type) | $Te^{6+}$, $I^{7+}$ | $[X^{n+}Mo_6O_{24}]^{-(12-n)}$ |

TABLE I-continued

Typical heteropolymolybdate anions

| CONDENSATION RATIOS | | HETERO ATOMS (X) | CHEMICAL FORMULAS |
|---|---|---|---|
| | (B type) | $Co^{3+}$, $Al^{3+}$, $Cr^{3+}$ | $[X^{n+}Mo_6O_{24}H_6]^{-(6-n)}$ |
| 4:12 | | $As^{5+}$ | $[H_4As_4Mo_{12}O_{52}]^{4-}$ |
| 2:5 | | $P^{5+}$ | $[P_2Mo_5O_{23}]^{6-}$ |

In the case of one step synthesis of ethers, suitable heteropoly acid catalysts may contain polyatoms selected from the group molybdenum, tungsten, niobium and vanadium, while the heteroatoms may be phosphorus, silicon, germanium, and arsenic. Preferably the heteroatoms are phosphorus or silicon. These heteropoly acids would likely have the Keggin structure, $H_{8-n}[XM_{12}O_{40}]$, where X=P or Si, M=Mo or W and n is an integer which is 4 or 5.

The preferred heteropoly acids for the practice of this invention include 12-molybdophosphoric acid, $H_3PMo_{12}O_{40}$, 12-tungstophosphoric acid, molybdosilicic acid, $H_4SiMo_{12}O_{40}$ and 12-tungstosilicic acid. Said acids are generally used as heterogeneous catalysts bonded to a suitable support.

The etherification portion of the catalyst preferably comprises a metal phosphate. The phosphates which are suitable for the supports in the catalyst of the instant invention comprise inorganic stoichiometric metal phosphates having special utility as heterogeneous catalysts. The metals may include: calcium, boron, iron, zirconium, cerium and chromium. The preferred metals are iron or boron.

The metal phosphates are prepared using metal salts. The metal salt may be any water-soluble salt of the metal desired which has the needed valence (oxidation state). Salts of strong acids are particularly suitable. Thus, for example, ferric nitrate, ferric sulfate and ferric chloride are appropriate. In general, +3 oxidation state transition metals produce the preferred catalytic properties —$Fe^{+3}$, $Cr^{+3}$, $Ce^{+3}$ and the like are preferred transition metals. The metal salt solution is usually dilute having 1 to 10% solids by weight.

The metal phosphate can comprise up to 100% of the etherification portion of the catalyst. Alternatively, the etherification portion of the catalyst can comprise 10% to 90% by weight iron or boron phosphate and 90% to 10% by weight of a metal oxide. Example 1 demonstrates the use of a Ni—Cu—Cr hydrogenation catalyst on a support comprising 100% by iron phosphate, while Example 4 demonstrates 80% SAPO-5 molecular sieve and 20% alumina.

The preferred phosphate is iron phosphate. The iron phosphate support can be prepared by first forming an aqueous solution of ferric irons (Fe+++). This is conveniently accomplished by adding a suitable ferric salt to a vessel containing water at room temperature and then adding an essentially stoichiometric amount of phosphoric acid, sufficient to utilize all of the ferric irons present. For example, 85% phosphoric acid can be used, however other concentrations can also be used.

As a source of ferric ions, it is desirable to employ a ferric salt that has a level of solubility in water which will allow the preparation of catalysts wherein the concentration of ferric phosphate on the alumina support material can be easily increased or decreased as desired. Representative ferric salts are ferric nitrate sextahydrate, ferric nitrate nonahydrate, ferric formate, ferric citrate, ferric bromide and ferric chloride.

The ferric salt/phosphoric acid solution is then mixed with alumina support material at room temperature to impregnate it. The impregnated alumina particles are usually dried at about 110° C. to provide a precatalyst. Relative proportions of impregnation solution and alumina support material are selected so as to ultimately provide the desired concentration of ferric phosphate on the support material.

While these compositions can be used without dilution or the use of a support, such dilution can be desirable for economic reasons or to enhance the physical properties of the final product. Thus, inert inorganic materials, particularly oxides such as silica, alumina, titania and the like can be physically mixed with the compositions at whatever stage of the preparation is most convenient. The inert "support" may be present at the point of gelation or precipitation. The level of diluent or support when employed may range from 10 to 90 w/w.

The mixing is usually carried out at ambient temperature, but a temperature as low as 0° C. and as high as 100° may enhance the physical properties of the product. Aging for a period of 1 to 24 hours at a temperature from about 25° C. to about 100° C. can also enhance the physical properties of the product. Adjustment of pH or salt content during such aging also can provide improved properties.

The phosphate solution may be prepared separately from the metal salt solution, or may be prepared at the same time if the required $PO_4/M$ mole ratio can be obtained without any reaction between the metal and phosphate. Suitable phosphate sources include orthophosphoric acid, ammonium phosphate, ammonium hydrogen phosphate and ammonium dihydrogen phosphate and the like. This solution is also dilute, having 1 to 10% solids by weight. Mixing of these solutions is accomplished by any convenient means. Both can be added individually to a third pH-adjusting solution or the combined metal/phosphate solution can be added to the pH-adjusting solution. The mixing must be done efficiently with relatively short mixing times to assure preparation of a homogeneous product.

The pH-adjusting solution is most conveniently dilute aqueous ammonia, but other alkaline materials may be suitable. The final pH of the mixture should be 3 to 11; preferably 7 to 11 and, most preferably, 8 to 10.

Depending upon the concentrations of ingredients in the impregnation solution, and the ferric phosphate concentration desired, more than one impregnation step may be required. The precise concentration of ferric phosphate is not critical in the sense of whether the process is or is not operational. For most operations, however, concentrations of ferric phosphate on the alumina support material will be in the range of about 1–20%, but preferably, in order to obtain good selectivity, about 11–14%. The level of active catalyst does not seem to have a dramatic effect on selectivity, but in combination with the other controllable variables, provides an additional means of controlling the process. It is generally accepted in the catalytic art that, where an alumina support material is one high in silica, it is often advantageous to incorporate a potassium salt, e.g., potassium nitrate, to reduce the acidic properties of such a support, especially where the material to be oxidized is relatively sensitive to hydrolysis under acidic conditions. In the present process the addition of small amounts of a potassium salt, such a potassium nitrate, may be added to the aqueous medium along with the ferric salt.

After the precatalyst is prepared it is subjected to a calcining operation wherein the precatalyst is heated in air. The air can be relatively static or an air sweep can be used. An air sweep furnace, e.g., a muffle furnace, has been found useful for the calcining operation. It has been found that for calcining, temperatures of the order of from about 400° C. to about 800° C. for from about 3 to about 6 hours give satisfactory results. Calcining at about 500°–600° C. for about 3–5 hours has been found to provide good results and is preferred. The catalysts may be used immediately or stored until needed. No special conditions of storage are required.

Where the metal in the phosphate is boron the catalyst can be prepared as described in U.S. Pat. No. 5,233,119 (Col. 3, Example 1), incorporated herein by reference in its entirety.

Generally the $BPO_4$ is prepared by adding with stirring over a period of about several hours a solution of a boric acid ester of the formula $B(OR)_3$ wherein each R can be independently selected from alkyl radicals containing 1–5 carbon atoms (such as, for example, tri-n-propyl borate) and 60–90 wt % orthophosphoric acid with $SiO_2$ either being absent during the reaction (so as to prepare a 100% $BPO_4$ material) or $SiO_2$ being present during this reaction in an amount as to provide a material containing up to about 80 wt % $SiO_2$ (preferably about 0.5–80 wt % $SiO_2$) at a temperature of about 80° C. under a nitrogen gas atmosphere.

The reaction mixture is heated under reflux conditions to a temperature of 120° C. and thereafter essentially all liquids (mainly water and propanol) are distilled off. The white solid residue of $BPO_4$ is vacuum dried at a temperature of about 120° C. for several hours to obtain dry boron phosphate.

Where the resulting material contains up to about 80 wt % $SiO_2$, generally a metal phosphate/Group III or IV oxide support can be prepared by placing 20–40 mesh silica and a mixture of about 85 wt % $H_3PO_4$ and 15% water into a 3 neck flask, heating to about 80° C. under a $N_2$ atmosphere and adding the boric acid ester dropwise, while stirring; heating the entire mixture for 2 hours under reflux conditions and, thereafter distilling off essentially all liquids at a temperature of about 120° C. Then the solid residue was dried for 3 hours at a temperature of about 150° C. under vacuum conditions.

The wt % of $BPO_4$ can be adjusted by adjusting the amount of added silica.

In another embodiment the catalyst support material can comprise large pore silicoaluminophosphates. These materials are both crystalline and microporous and exhibit properties which are characteristic of both the aluminosilicate zeolites and the aluminophosphates of Wilson et al., supra. Members of this class of silicoaluminophosphate materials have a three-dimensional microporous crystal framework structure of $PO_2^+$, $AlO_2^-$ and $SiO_2$ tetrahedral units, the essential empirical chemical composition of which on an anhydrous basis is:

mR: $(Si_xAl_yP_z)O_2$ wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume of the pore system of the particular silicoaluminophosphate species involved, "x", "y" and "z" represent the mole fractions of silicon, aluminum and phosphorus, respectively, present as tetrahedral oxides, said mole fractions being such that they are within a pentagonal compositional area.

These SAPO compositions and the method of preparing them are described in U.S. Pat. No. 4,440,871, mentioned above and incorporated.

Forming of the catalyst into the sizes and shapes of particles most suited to a particular application can be done by techniques well-known in the art. Thus, spray drying, extrusion, pelleting or various spheroidization methods are effective. Inclusion of a diluent can be beneficial. Forming or dilution can be done at various stages of the preparation as dictated by the requirements of the specific forming method chosen. Suitable diluents well-known in the art can be used, but silica has been found to be particularly suitable.

In most cases the catalysts will be used as regular shapes such as microspherical beads, larger beads, or particles with cylindrical cross-sections as are commonly used in heterogeneous catalysis, although they can be prepared as irregular powders or granules.

The reaction may be carried out in either a stirred slurry reactor or in a fixed bed continuous flow reactor. The catalyst concentration should be sufficient to provide the desired catalytic effect.

Dehydration/etherification to DIPE, MTBE or IPTBE can generally be conducted at temperatures from 20° to 250° C.; the preferred range is 50° to 200° C. Good results are observed throughout this temperature range. However, it can be noted that the best conversion figures for MTBE, DIPE cogeneration are observed when the temperature is 210°–290° F. (99° C.–143° C.). The total operating pressure may be from 0 to 5000 psig, or higher.

The preferred pressure range is 100 to 1000 psi.

The selectivity for the formation of DIPE and IPTBE can be adjusted by reaction temperature. DIPE formation is favored at higher reaction temperatures whereas, IPTBE is favored at lower temperatures. Table 2 illustrates the influence of temperature on the selectivities of DIPE and IPTBE.

TABLE 2

| ONE-STEP IPTBE SYNTHESIS | | | | |
|---|---|---|---|---|
| Temp. (°C.) | Catalyst | tBA Conv. % | MTBE wt % | DIPE wt % | IPTBE wt % |
| 80° C. | Amberlyst 15, A | 24 | | 0.1 | 15.3 |
| 80° C. | Amberlyst 15, B | 34 | 18.4 | | 7.3 |
| 80° C. | H-Beta, B | 44 | 17.3 | | 7.3 |
| 80° C. | H-Beta, A | 25 | | 0.1 | 14.7 |
| 140° C. | H-Beta, A, 140 | 98 | | 16.9 | 0.2 |
| Feed A: 33 wt % IPA, 67 wt % tBA | | | | | |
| Feed B: 11% MA, 29 wt % IPA, 58% tBA | | | | | |

With feed A both Amberlyst 15 and Beta zeolite catalysts give 0.1 wt % DIPE and 15% IPTBE at 80° C. When the temperature is raised to 140° C., the DIPE yield is increased to 16.9 wt % and IPTBE decreases to 0.2wt %.

Similarly, with feed B both catalysts gave about 17–18 wt % MTBE and 7.3 wt.% IPTBE at 80° C. The formation of MTBE is favored at a temperature range of 80° C.–160° C. By contrast IPTBE is most favored at 40°–70° C.

Therefore the temperature required for maximizing the ether selectivity follows the order of

IPTBE<MTBE<DIPE

Typically, IPA and DIPE are generated continuously in up to ca. 98 wt % concentration or greater in the crude liquid product at total liquid hourly space velocities (LHSV) of up to 10 or higher and relatively mild conditions, where:

$$LHSV = \frac{\text{Volume Of Total Liquid Feed Run Through The Reactor Per Hour}}{\text{Volume of Catalyst In Reactor}}$$

Conversions of acetone are estimated in the following examples using the equation:

$$\frac{(\text{Mole \% of Acetone in Feed} - \text{Mole \% of Acetone in Product})}{\text{Mole \% of Acetone in Feed}} \times 100$$

The following examples are merely illustrative of the preferred embodiment. Many variations thereon may be made without departing from the spirit of the disclosed invention, as will be evident to those skilled in the art.

EXAMPLE 1

(Example of Invention)

The catalyst of Example 1 was a Ni/Cu/Cr Iron Phosphate catalyst having a 59/21/2/18 mole ratio of Ni/Cu/Cr/Fe.

The catalyst screening run for Example 1 was performed in a microreactor test unit. The reactor was operated in a downflow configuration and had two catalyst beds of 4 cc each, separated by a 4 cc bed of inert material. The total charge of catalyst was 8 cc in the unit. Internal thermocouples were positioned at the bottom of each catalyst bed. The liquid feed was charged to the unit using a high pressure pump and the hydrogen was metered through a mass flow controller. For the purpose of simplifying the analysis of liquid products by GC, pure acetone (technical grade, 97%) was used as a feedstock to demonstrate the chemistry involved in the instant invention.

The catalysts were activated by heating slowly from room temperature to 600° F. over a 6 hour period under flowing nitrogen at 70 psig. The unit pressure was then raised to 500 psig with hydrogen and the catalyst bed was held at 600° F. for 10 hours under flowing hydrogen. The catalyst bed was cooled down to below 200° F. The acetone feed was charged to the unit at 1.5 LHSV based on total catalyst volume. The hydrogen flow rate was controlled to give a hydrogen to acetone mole ratio of 5:1 and a total pressure of 500 psig. The acetone feed was mixed with hydrogen prior to entering the reactor. The liquid product was collected periodically in a chilled receiver at 5° F. and 300 psig. The product was analyzed by GC to determine the composition of hydrocarbons and oxygenates.

EXAMPLE 2

(Comparative Example)

A 50g batch of 80% ETAS-10/20% alumina support (052-92-2003-000) was impregnated with a 45 cc aqueous solution containing 51 g of nickel nitrate hexahydrate and 5.4 g of copper nitrate hemipentahydrate. The impregnated support was dried at 250° F./2 hours, and then calcined at 600° F./4 hours. The calcined support was impregnated again with a 40 cc aqueous solution containing 51 g of nickel nitrate hexahydrate and 5.4 g of copper nitrate hemipentahydrate. The impregnated support was dried at 250° F./2 hours, and then calcined at 900° F./8 hours. The finished catalyst, Example 2 (052-93-6919-115), contains 28% Ni and 4% Cu.

The catalyst screening run for Example 2 was performed in a microreactor test unit which has two reactors in series separated by a quench zone. The reactors were operated in a downflow configuration. The top reactor was loaded with a 4 cc catalyst. The second reactor has two catalyst beds of 4 cc of catalyst each separated by a 4 cc bed of inert material. The total charge of catalyst was 12 cc in the unit. Internal thermocouples were positioned at the bottom of each catalyst bed. The liquid feed was charged to the unit using a high pressure pump and the hydrocarbon was metered through a mass flow controller. Both hydrogen and liquid feedstock were mixed and charged to the unit. For the purpose of simplifying the analysis of liquid products by GC., pure acetone was used as a feedstock to demonstrate the chemistry involved in the instant invention.

The catalysts were activated by heating slowly from room temperature to 600° F. over a 6 hour period under flowing nitrogen at 70 psig. The unit pressure was then raised to 500 psig with hydrogen and the catalyst bed was held at 600° F. for 10 hours under flowing hydrogen. The catalyst bed was cooled down to below 200° F. The acetone feed was charged to the unit at 1.0 LHSV based on total catalyst volume. The hydrogen flow rate was controlled to give a hydrogen to acetone mole ratio of 5:1 and a total pressure of 500 psig. The acetone feed was mixed with hydrogen prior to entering the reactor. The liquid product was collected periodically in a chilled receiver at 5° F. and 300 psig. The product was analyzed by GC to determine the composition of hydrocarbons and oxygenates.

EXAMPLE 3

(Comparative Example)

A 50 g of 60% B-zeolite/40% alumina support was impregnated with a 40 cc aqueous solution containing 51 g of nickel nitrate hexahydrate and 5.4 g of copper nitrate hemipentahydrate. The impregnated support was dried at 250° F./2 hours, and then calcined at 600° F./4 hours. The calcined support was impregnated again with a 37 cc aqueous solution containing 51 g of nickel nitrate hexahydrate and 5.4 g of copper nitrate hemipentahydrate. The impregnated support was dried at 250° F./2 hours and then calcined at 900° F./8 hours. The finished catalyst, Example 3 (052-93-6896-021), comprises 28% Ni and 4% Cu. The catalyst screening run was carried out as described in Example 2.

Other catalysts with similar properties to those of Example 1 which will be useful in this process are supported heteropoly acids, such as $H_3[PMo_{12}O_{40}]/SiO_2.Al_2O_3$ and $H_3[PW_{12}O_{40}]/SiO_2$, boron phosphates, such as $H_3PO_4.H_3BO_3/SiO_2$, large pore silicoaluminophosphates (SAPO), such as SAPO-5, SAPO-37 and substituted SAPOs, such as MeAPSO-36.

EXAMPLE 1
Run No. 097-93-6025
Catalyst: 061-93-1024-600 Ni/Cu/Cr/FePO$_4$

| Cut. No. | TOS Hr. | Avg. Temp. | Liquid Recov. wt % | C$_3$ wt % | Acetone wt % | IPA wt % | DIPE wt % | C$_6$/C$_9$ wt % |
|---|---|---|---|---|---|---|---|---|
| 100 | 27 | 385 | 100 | 1.6 | 4.6 | 82.5 | 10.9 | 0.5 |
| 200 | 33 | 360 | 100 | 0.8 | 1.0 | 88.5 | 9.7 | 0.0 |

EXAMPLE 2
Run No. 097-93-6029
Catalyst: 052-93-6919-115 Ni/Cu/ETAS-10

| Cut. No. | TOS Hr. | Avg. Temp. | Liquid Recov. wt % | C$_3$ wt % | Acetone wt % | IPA wt % | DIPE wt % | C$_6$/C$_9$ wt % |
|---|---|---|---|---|---|---|---|---|
| 100 | 11 | 270 | 100 | 0 | 0 | 100 | 0 | 0 |
| 200 | 17 | 291 | 100 | 0 | 0 | 100 | 0 | 0 |

EXAMPLE 3
Run No. 097-93-6018
Catalyst: 052-93-6896-021 Ni/Cu/60% Beta

| Cut. No. | TOS Hr. | Avg. Temp. | Liquid Recov. wt % | C$_3$ wt % | Acetone wt % | IPA wt % | DIPE wt % | C$_6$/C$_9$ wt % |
|---|---|---|---|---|---|---|---|---|
| 600 | 8 | 294 | 25 | Liquid product was 90+% water | | | | |

EXAMPLE 4

The catalyst of example 4 is SAPO-5 (052-94-2338-000).

The catalyst screening run for example 4 was performed in a microreactor test unit. The reactor was loaded with 8 cc of catalyst and operated in a downflow configuration. An internal thermocouple was positioned at the bottom the catalyst bed. The liquid feed was charged to the unit using a high pressure pump. For the purpose of simplifying the test procedure and product analysis, pure isopropyl alcohol (IPA) was used as a feedstock. This example demonstrates the usefulness of SAPO materials to carry out the etherification chemistry involved in the instant invention.

The catalyst was activated by heating slowly from room temperature to 600° F. and held for 16 hours under flowing nitrogen. After drying, the reactor temperature was lowered to the desired start of run temperature. The IPA feed was charged to the unit at 1.5 LHSV based on catalyst volume and the unit was operated at a pressure of 300 psig. The liquid product was collected periodically in a chilled receiver at 5° F. and 350 psig. The product as analyzed by GC to determine the composition of hydrocarbons and oxygenates.

EXAMPLE 4
Evaluation of the Etherification Activity of SAPO-5

| Reaction Temperature °F. | IPA Conversion wt % | Yield DIPE wt % |
|---|---|---|
| 206 | 1.7 | 1.1 |
| 245 | 3.9 | 3.1 |
| 288 | 11.6 | 10.2 |
| 331 | 28.1 | 25.2 |
| 364 | 37.3 | 33.9 |

Note concerning Example 4:
The chemistry involved in the invention is:

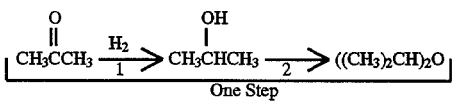

One Step

The chemistry of the 1st reaction is generally accomplished using metals, however reaction #2 is the challenge. The novelty of the instant invention is the combination of the two steps with a single catalyst.

Example 4 demonstrates the utility of SAPO materials for etherification reactions by carrying out reaction #2.

What is claimed is:

1. A one-step method for synthesis of methyl tertiary butyl ether, diisopropyl ether and isopropyl t-butyl ether from crude streams containing acetone, methanol and t-butyl alcohol which comprises reacting acetone-rich feed over a bifunctional catalyst consisting essentially of 5–45% by weight of a hydrogenation catalyst selected from one or more metals selected from the Group IB, VIB or VIII of the Periodic Table and a heteropoly acid on 55%–95% by weight of a support selected from the group consisting of:

a. a metal phosphate;

b. 5 to 95 wt % metal phosphate supported on 95 to 5 wt % Group III or IV oxide; and c. a large pore silicoaluminophosphate.

2. The method of claim 1 wherein the metals comprising the hydrogenation catalyst are selected from the group consisting of platinum, palladium, nickel, copper, tin and chromium.

3. The method of claim 1 wherein the Group IB metal is copper, the Group VIB metal is chromium and the Group VIII metal is nickel.

4. The method of claim 1 wherein the hydrogenation component is a heteropoly acid selected from $H_3[PMo_{12}O_{40}]$ and $H_3[PW_{12}O_{40}]$.

5. The method of claim 3 wherein the ratio of Ni/Cu/Cr/Fe is in the range of 50–70/15–25/0.5–5/15–25 respectively.

6. The method of claim 5 wherein the ratio of Ni/Cu/Cr/Fe is 55–60/18–22/1–4/16–20 respectively.

7. The method of claim 6 wherein the ratio of Ni/Cu/Cr/Fe is 59/21/2/18 respectively.

8. The method of claim 1 wherein the support is a metal phosphate selected from the group consisting of iron, phosphate and boron phosphate.

9. The method of claim 1(b) for synthesis of ethers from crude acetone streams wherein the support is selected from iron phosphate on silica, iron phosphate on alumina and boron phosphate on alumina.

10. The method of claim 1(c) wherein the large pore silicoaluminophosphate is selected from SAPO-5, SAPO-37 and substituted SAPOs.

11. The method of claim 10 wherein the substituted SAPO is MeAPSO-36.

12. The method of claim 1 wherein the temperature ranges from 50° C. to 200° C.

13. The method of claim 1 wherein the hydrogen pressure is about 100 psig to 1000 psig.

14. The method of claim 1 wherein the liquid hourly space velocity ranges from about 0.1–10.

15. The method of claim 1 wherein the formation of isopropyl tertiary butyl ether is favored at temperatures in the range 40°–70° C.

16. The method of claim 1 wherein the formation of methyl tertiary butyl ether is favored in the temperature range of 80° C.–160° C.

17. The method of claim 1 wherein the formation of diisopropyl ether is favored at temperatures above 140° C.

* * * * *